(12) United States Patent
Washington et al.

(10) Patent No.: US 10,064,799 B2
(45) Date of Patent: *Sep. 4, 2018

(54) SHAPING KERATIN FIBRES USING CARBONATE ESTER

(71) Applicant: The Procter & Gamble Company, Cincinnati, OH (US)

(72) Inventors: Randy Purnell Washington, West Chester, OH (US); Andreas Flohr, Kronberg (DE); David Frederick Swaile, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/577,186

(22) Filed: Dec. 19, 2014

(65) Prior Publication Data

US 2015/0174037 A1 Jun. 25, 2015

Related U.S. Application Data

(60) Provisional application No. 61/918,165, filed on Dec. 19, 2013.

(51) Int. Cl.

| A61K 8/60 | (2006.01) |
|---|---|
| A61K 8/33 | (2006.01) |
| A61K 8/49 | (2006.01) |
| A45D 7/06 | (2006.01) |
| A61Q 5/06 | (2006.01) |
| A61K 8/37 | (2006.01) |

(52) U.S. Cl.
CPC .......... *A61K 8/60* (2013.01); *A45D 7/06* (2013.01); *A61K 8/33* (2013.01); *A61K 8/37* (2013.01); *A61K 8/498* (2013.01); *A61K 8/4973* (2013.01); *A61Q 5/06* (2013.01); *A61K 2800/30* (2013.01); *A61K 2800/81* (2013.01); *A61K 2800/882* (2013.01); *A61K 2800/95* (2013.01)

(58) Field of Classification Search
None
See application file for complete search history.

(56) References Cited

U.S. PATENT DOCUMENTS

| 6,488,920 B1 * | 12/2002 | Thomas | A61K 8/20 424/70.1 |
|---|---|---|---|
| 8,349,780 B2 | 1/2013 | Baker | |
| 8,883,710 B2 | 11/2014 | Willey | |
| 2004/0156800 A1 | 8/2004 | Brun | |
| 2005/0048018 A1* | 3/2005 | Fadeeva | A61K 8/60 424/70.13 |
| 2005/0196369 A1* | 9/2005 | Ueyama | A61K 8/35 424/70.2 |
| 2009/0285768 A1* | 11/2009 | Baker | A61K 8/361 424/59 |
| 2010/0310491 A1* | 12/2010 | Falk | A61K 8/06 424/70.122 |
| 2013/0319449 A1* | 12/2013 | Xavier | A61Q 5/002 132/209 |
| 2015/0096584 A1 | 4/2015 | Washington | |
| 2015/0128984 A1 | 5/2015 | Paul et al. | |
| 2015/0173478 A1 | 6/2015 | Adams | |
| 2015/0173479 A1 | 6/2015 | Adams | |
| 2015/0173480 A1 | 6/2015 | Washington | |
| 2015/0174023 A1 | 6/2015 | Washington | |
| 2015/0174027 A1 | 6/2015 | Washington | |
| 2015/0174028 A1 | 6/2015 | Washington | |
| 2015/0174029 A1 | 6/2015 | Washington | |
| 2015/0174030 A1 | 6/2015 | Washington | |
| 2015/0174031 A1 | 6/2015 | Washington | |
| 2015/0174032 A1 | 6/2015 | Washington | |
| 2015/0174035 A1 | 6/2015 | Reed | |
| 2015/0174036 A1 | 6/2015 | Washington | |
| 2015/0174432 A1 | 6/2015 | Adams | |
| 2015/0174793 A1 | 6/2015 | Adams | |
| 2015/0374604 A1 | 12/2015 | Kadir | |

FOREIGN PATENT DOCUMENTS

| JP | 2007176796 A | 7/2007 |
|---|---|---|
| WO | WO2013117770 A2 | 8/2013 |
| WO | WO2013117843 A1 | 8/2013 |
| WO | WO2015069823 A1 | 5/2015 |

OTHER PUBLICATIONS

National Center for Biotechnology Information. PubChem Compound Database; CID=7303, <https://pubchem.ncbi.nlm.nih.gov/compound/7303> (accessed Jan. 11, 2016).*

* cited by examiner

*Primary Examiner* — Nicole P Babson
(74) *Attorney, Agent, or Firm* — Alexandra S. Arnoff

(57) ABSTRACT

A method for shaping keratin fibers comprising: providing a crosslinking composition, wherein the crosslinking composition comprises: an active agent, wherein the active agent is a carbonate ester; a cosmetically acceptable carrier; and applying the crosslinking composition to keratin fibers, mechanically shaping the keratin fibers with an appliance at a temperature of from about 50° C. to about 250° C. Also a related composition, use, kit and process.

3 Claims, 1 Drawing Sheet

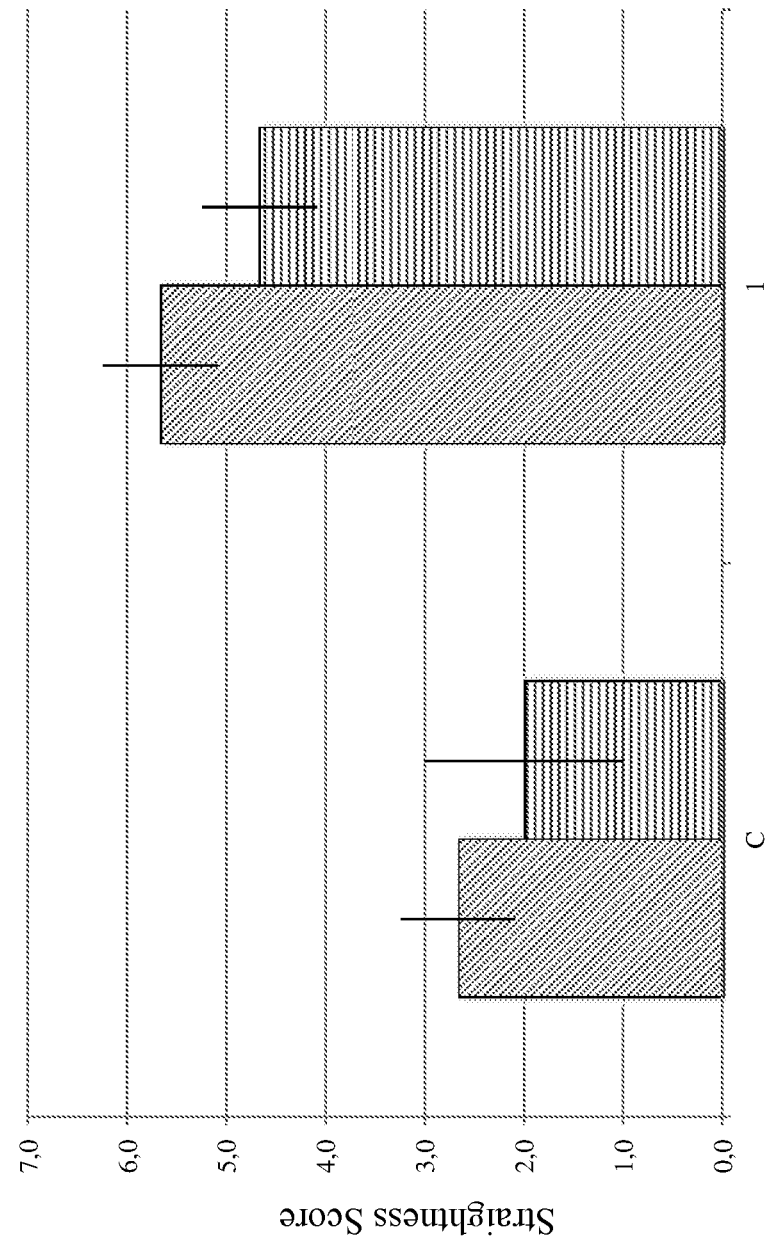

SHAPING KERATIN FIBRES USING CARBONATE ESTER

FIELD OF THE INVENTION

A method for shaping keratin fibres comprising: providing a crosslinking composition, wherein the crosslinking composition comprises: an active agent, wherein the active agent is a carbonate ester; a cosmetically acceptable carrier; and applying the crosslinking composition to keratin fibres, mechanically shaping the keratin fibres with an appliance at a temperature of from about 50° C. to about 250° C.

BACKGROUND OF THE INVENTION

Consumers are constantly demanding products that meet their daily styling and conditioning needs without damaging the hair. The perceived and sometimes real impact of various treatments and the implements such as blow drying and flat iron can have detrimental effects on the acute and chronic nature of hair.

Permanent methods—or relaxers—usually comprise the steps of applying onto hair a composition comprising a high pH solution (or combination of components to generate high pH), leaving on for a protracted time and then applying a neutralizing composition. A relaxer is a treatment predominately used by people of African-descent to permanently straighten hair. The treatment relies on either the one-step sodium hydroxide (lye) or a two step (e.g. guanidine carbonate and calcium hydroxide) to achieve very high pH (pH 12-14).

Semi-permanent benefits can be achieved using redox chemistry such as thioglycolic acid (TGA) and hydrogen peroxide. Here, the curly hair is transformed into the straight hair because the disulfide bonds are broken by the reaction with TGA. The straighter style is locked in during the oxidation step with hydrogen peroxide.

Non-permanent methods usually comprise the step of heating the hair with a flat-iron or heating element. Methods using such devices in combination with chemically-modifying the internal hair fibres can obtain long-lasting effects e.g. over several months. The Brazilian Keratin Treatments (BKTs) enable the achievement of a straight hairstyle that lasts several months via a shampoo treatment. The key active in BKTs is formaldehyde. The most efficacious treatments (used mainly in salons) rely on high temperature—usually 232° C. (450° F.)—with formaldehyde. Hair treated with products with high concentration of formaldehyde such as Brazilian Blowout delivers semi-permanent straight hair. Over time and following shampooing, the hair reverts back to a curly configuration.

The known methods for straightening hair all have drawbacks. The permanent methods are typically time-consuming and may damage hair. In addition, such methods show little flexibility so that any need and/or wish for changing the hairstyle would require conducting again a "permanent" wave onto hair, which is time-consuming and further damages the hair.

Along with the high potential skin irritation during application, relaxers tend to permanently change the hair by breaking the natural disulfide bonds in the hair. This leaves the hair weaker and more prone for further breakage. Overprocessing can also increase hair damage and skin irritation. Consumer products using redox chemistry to achieve semi-permanent benefits, but overprocessing the hair and the strong sulphur smell are concerns of technologies based on reducing chemistry.

According to the US National Toxicology Program, formaldehyde is known to be a human carcinogen. Therefore, providing a semi-permanent style with carcinogen-free formulation is paramount. Given the safety concern of formaldehyde and the damaging effect of relaxers and reducing chemistry, there is a need for a safe alternative to durable straightening that does not break disulfide bonds.

None of the above methods allow achieving a hairstyle that may be retained and/or recovered after at least one shampoo treatment without severely damaging the hair or using a carcinogenic active. There is a need for the provision of a method for achieving a hairstyle that lasts at least five shampoo treatments so that the user would not need to re-shape hair after each shampoo but would still have the opportunity to change hairstyle after some time and without needing to use stringent or harsh hair treatment, such as the permanent technologies outlined above.

WO2009/140076A1 states: a composition including an active material having functional groups capable of covalent attachment to a substrate in the presence of an acid or a base, a photocatalyst capable of generating an acid or a base upon exposure to light, and a vehicle. WO2011/074143A1 (De Boni et al) states: a process for treating keratin fibers comprising the steps of: applying onto the keratin fibers a composition comprising at least one saccharide or derivative thereof; then placing the keratin fibers in an occlusive space; and then heating the keratin fibers, wherein the composition contains neither a reducing agent nor a source of carbonate ions of the formula: wherein X is a group selected from the group consisting of O, OH, NH2, O— OH, and O—COO. US2007/0226916A1 (Mellul et al) discloses a composition which, in a preferred embodiment, contains, in a cosmetically acceptable medium, at least one monosaccharide and/or disaccharide, at least one a-hydroxy acid, and at least one ceramide compound.

There is a need therefore for providing a method for achieving and semi-permanently retaining and/or recovering hairstyle using actives that do not break disulfide bonds (reducing agents) or that are considered carcinogenic. There is also the need for providing a method for obtaining a hairstyle exhibiting resistance to shampoo treatments. Particularly, there is a need for providing a method for retaining and/or recovering hairstyle after at least one shampoo treatment, particularly after five shampoo treatments, more particularly after ten shampoo treatments. In addition, there is a need for providing a method for achieving and retaining and/or recovering hairstyle, without damaging hair. Also, there is a need for providing more economic semi-permanent hair straightening or hair relaxing treatments.

SUMMARY OF THE INVENTION

A first aspect of the invention relates to a method for shaping keratin fibres comprising:
  (a) providing a crosslinking composition, wherein the crosslinking composition comprises:
    an active agent, wherein the active agent is a carbonate ester; and wherein the active agent has a molecular weight of 500 g/mol or less;
    a cosmetically acceptable carrier;
  (b) applying the crosslinking composition to keratin fibres, mechanically shaping the keratin fibres with an appliance at a temperature of from about 50° C. to about 250° C.

A second aspect of the invention relates to a crosslinking composition for shaping keratin fibres comprising:

an active agent, wherein the active agent is a carbonate ester; and wherein the active agent has a molecular weight of 500 g/mol or less;

a sugar, or a reducing sugar;

optionally a cosmetically acceptable carrier.

A third aspect of the invention relates to the use of the crosslinking composition according to the second aspect for shaping keratin fibres.

A fourth aspect of the invention relates to a kit comprising:
(a) a crosslinking formulation comprising an active agent, wherein the active agent is a carbonate ester; and wherein the active agent has a molecular weight of 500 g/mol or less;
(b) an appliance for mechanically shaping keratin fibres; wherein each of (a) and (b) are separately packaged.

A fifth aspect of the invention relates to a process for forming a crosslinking composition, comprising mixing together:

an active agent, wherein the active agent is a carbonate ester; and wherein the active agent has a molecular weight of 500 g/mol or less; and a sugar or a reducing sugar; and a cosmetically acceptable carrier.

BRIEF DESCRIPTION OF THE DRAWINGS

FIG. 1: Shows hair straightness analysis presented as a bar chart. The left hand bar (shaded) shows the straightening efficacy after 1 performance wash and the right hand bar (horizontal stripes) shows the straightening efficacy after 10 performance washes. C=control experiment and 1=after treatment with crosslinking composition of the present invention. Hair without treatment with the crosslinking composition of the present invention shows less straightening (lower scale) than treated hair with crosslinking composition of the present invention (the active agent is 1,3-dioxolan-2-one).

DETAILED DESCRIPTION OF THE INVENTION

Definitions and General

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 25° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein: "min" means "minute" or "minutes"; "mol" means mole; "nanometers" is abbreviated "nm"; "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially or. The compositions, formulations, methods, uses, kits, and processes of" the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from about 1% to about 5% fatty alcohol, then a composition comprising 2% stearyl alcohol and 1% cetyl alcohol, would fall within the scope.

"Molecular weight" or "M.Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than about 1%, or less than 0.8%, or less than 0.5%, or less than 0.3%, or about 0%, by total weight of the composition or formulation.

"Keratin fibres" means fibrous material composed of keratin. "Hair" means mammalian keratin fibres including scalp hair, facial hair and body hair. It includes such hair still being attached to a living subject and also hair that has been removed therefrom such as hair switches and hair on a doll/mannequin. In at least one embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

Description

The present invention relates inter alia to a method for shaping keratin fibres. The present method allows the achievement of a semi-permanent hairstyle i.e. a durable hairstyle, and semi-permanent shaping of eyelashes. This semi-permanent hairstyle is retained after at least one shampoo treatment, particularly after five shampoo treatments, more particularly after 10 shampoo treatments. Besides the increased durability of the hairstyle, this method prevents clumping of hair and/or improves post-shampoo detangling of hair and feel. In addition, the inventors have found that this method increases the water- and humidity-resistance of the shape, increases the ease of style and/or increases the manageability of the shape after shampooing. Without wishing to be bound by any theory, it is believed that the above benefits are due to the steps conducted, their sequence, as well as the specific components used including the active agent. It is believed that the selected active agent diffuses into the shaft of the keratin fibre, reacts with carboxylic acid or other acid groups to form crosslinks in the keratin polypeptide, providing sufficient crosslinks to overcome the innate restoring force of the keratin fibre structure. This results in a durable shaping of keratin fibres, for example a durable hairstyle or durable eyelash shape.

The details of the different aspects of the invention are described hereinafter. The present invention relates inter alia to a method for shaping keratin fibres. The method comprises providing a crosslinking composition.

Crosslinking Composition

The crosslinking composition comprises an active agent. The active agent is useful for reacting with and providing crosslinks in keratin. The active agent is a carbonate ester; and wherein the active agent has a molecular weight of 500 g/mol or less. In at least one embodiment, the active agent has a molecular weight of 300 g/mol or less, of 400 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the carbonate ester conforms to the formula $R_1O(C=O)OR_2$ wherein $R_1$ and $R_2$ are independently a $C_{1-18}$ alkyl, alkylene, or phenyl, which includes cyclic, non-cyclic, branched chain and straight chain. In at least one embodiment, the carbonate ester conforms to the formula $R_1O(C=O)OR_2$ wherein $R_1$ and $R_2$ are independently a $C_{1-10}$ alkyl or alkylene. In at least one embodiment, the carbonate ester conforms to the formula $R_1O(C=O)OR_2$ wherein $R_1$ and $R_2$ are independently selected from: methyl, ethyl, and phenyl. In at least one embodiment, the carbonate ester is selected from the group consisting of: 1,3-dioxolan-2-one; dimethyl carbonate; diethyl carbonate; diphenyl carbonate; 1,3-dioxan-2-one (trimethylene carbonate); 4-methyl-1,3-dioxolan-2-one; and mixtures thereof.

In at least one embodiment, the active composition comprises from about 0.1% to about 40% active agent. In at least one embodiment, the composition comprises from about 0.5% to about 20%, or from about 0.1% to about 15%, or from about 1% to about 12%, or from about 5% to about 15%, or from about 10% to about 12% active agent. In at least one embodiment, the crosslinking composition comprises a total amount of active agent (which includes any second active agent, where present) and wherein the total amount of active agent is from about 0.1% to about 40% active agent.

In at least one embodiment, the crosslinking composition comprises a cosmetically acceptable carrier. In at least one embodiment, the cosmetically acceptable carrier is any carrier suitable for formulating the active agent into a crosslinking composition being suitable for application onto hair. In at least one embodiment, the cosmetically acceptable carrier is selected from either an aqueous medium or an aqueous-alcoholic medium. In at least one embodiment, when the carrier is an aqueous-alcoholic carrier, this carrier comprises water and an alcohol. In at least one embodiment, the alcohol is selected from the group consisting of: ethanol, isopropanol, propanol, and mixtures thereof. In at least one embodiment, when the carrier is an aqueous carrier, this carrier consists essentially of water and is substantially free of alcohol. In at least one embodiment, the crosslinking composition comprises a safe and effective amount of cosmetically acceptable carrier. In at least one embodiment, the crosslinking composition comprises from about 0.1% to about 99%, or from about 1% to about 98%, or from about 10% to about 97%, or from about 30% to about 95% water.

In at least one embodiment, the crosslinking composition further comprises a second active agent. The second active agent is useful for reacting with and providing further crosslinks in keratin. The hair comprises polypeptides of keratin having functional groups COOH, OH, and $NH_2$, and SH. Different active agents can react preferentially with each functional group. For instance, arabinose preferentially reacts with amino groups whereas ethylene carbonate reacts preferentially with COOH. In at least one embodiment, the second active agent has at least two functional groups selected from the group consisting of: —$NH_2$, —NH—, —SH, —OH, —C(=O)H, —C=O, and —COOH; and wherein the second active agent has a molecular weight of 500 g/mol or less. In at least one embodiment, the second active agent is a sugar. Sugars are useful because they are naturally-derived, which is preferred by consumers versus synthetic compounds. This is not only for perceived health and lack of sensitisation reasons, but also for sustainability and environmental reasons—sugars break down naturally and quickly and do not require special disposal methods. Furthermore, sugars are also easy to source and relatively inexpensive. In at least one embodiment, the second active agent has a molecular weight of 500 g/mol or less. In at least one embodiment, the second active agent has a molecular weight of 300 g/mol or less, or from about 50 g/mol to 250 g/mol, or from about 80 g/mol to about 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle. In at least one embodiment, the second active agent is liquid at 25° C. Second active agents being liquid at this temperature have the advantage of providing improved hair feel versus second active agents that are solid at this temperature.

In at least one embodiment, the crosslinking composition further comprises a second active agent being a sugar or a reducing sugar. In at least one embodiment, the second active agent is a monosaccharide. In at least one embodiment, the sugar is a monosaccharide and wherein the crosslinking composition comprises from about 0.1% to about 40%, or from about 0.5% to about 20%, or from about 1% to about 15%, or from about 7% to about 20%, or from about 8% to about 19%, or from about 10% to about 18% monosaccharide. In at least one embodiment, the second active agent is a pentose, tetraose, hexose, derivative thereof, or mixture thereof. Derivatives may be acetyl derivatives. In at least one embodiment, the sugar is an acetyl derivative of a monosaccharide. In at least one embodiment, second active agent is a reducing sugar. In at least one embodiment, the crosslinking composition comprises from about 7% to about 20%, or from about 8% to about 19%, or from about 10% to about 18% reducing sugar. In at least one embodiment, the crosslinking composition comprises from about 12% to about 18% reducing sugar. In at least one embodiment, the crosslinking composition comprises a reducing sugar and wherein, if the crosslinking composition is heated to a temperature of 100° C., the crosslinking composition comprises from about 12% to about 18% reducing sugar. In at least one embodiment, the crosslinking composition comprises a total amount of reducing sugar being from about 12% to about 18% reducing sugar.

As used herein, "reducing sugar" means any sugar that either has an aldehyde group or is capable of forming an aldehyde group in solution through isomerism, and that gives a positive result in the Benedict's test. An aldehyde group is —C(=O)H. The aldehyde group is important in view of reacting with and crosslinking the hair. The Benedict's test involves employment of the Benedict's solution. The Benedict's solution is available from Sigma Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive Benedict's test result is confirmed with a change in colour as cupric ions ($Cu^{2+}$) are converted to cuprous ions i.e. reduced to copper(I) ions ($Cu^+$). These are precipitated as red copper(I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength of light reflected by the solution will change with the colour. In at least one embodiment, a positive Benedict's test result is when the solution emits light not peaking with a wavelength in the range of 450 nm to 495 In at least one embodiment, a positive Benedict's test result is when the solution emits light peaking with a wavelength in the range of 620 nm to 750 nm. This can be measured using a spectrophotometer,

TABLE 1

Assessment of sugars using the Benedict's Test

| Sugar | 80° C., 15 min | 100° C., 40 min |
|---|---|---|
| Control solution* | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In the art, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One litre of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In at least one embodiment, where if the crosslinking composition is heated to a temperature of at least 100° C., the crosslinking composition comprises from about 6% to about 20% reducing sugar. What is meant by "if the crosslinking composition is heated to a temperature of at least 100° C., the crosslinking composition comprises from about X % to about Y % reducing sugar" is that if the crosslinking composition was heated to a temperature of at least 100° C., the crosslinking composition would thereafter comprise reducing sugar within the prescribed percentage range. This is in view of the heat energy causing chemical change in the sugar (e.g. degradation) that results in the formation of reducing sugar in the crosslinking composition. This is where the method comprises elevating the temperature of the appliance to a temperature of at least 100° C. and mechanically shaping the keratin fibres with the appliance, which would cause the chemical change in the sugar (e.g. degradation) that results in the formation of reducing sugar in the crosslinking composition. In at least one embodiment, the "heated to a temperature of at least 100° C." is carried out for from 2 sec to 10 min, or from 1 min to 5 min, or from 2 min to 3 min. In at least one embodiment, the crosslinking composition comprises a reducing sugar and wherein, if the crosslinking composition is heated to a temperature of at least 100° C., the crosslinking composition comprises from about 12% to about 18% reducing sugar. In at least one embodiment, the crosslinking composition comprises sucrose, a buffering agent, and a cosmetically acceptable carrier; and wherein, where the crosslinking composition is heated to a temperature of at least 100° C., the crosslinking composition comprises from about 6% to about 20% reducing sugar. Sucrose is able to break down into reducing sugar following heating. A similar effect is obtained with O-methyl glycosides, isopropylidenes, and benylidenes. In at least one embodiment, the active agent is a O-methyl glycoside, isopropylidene, or a benylidene. In at least one embodiment, the sugar is a glucoside. In at least one embodiment, the sugar is methyl glucoside. In at least one embodiment, the sugar is a disaccharide. In at least one embodiment, the sugar is sucrose.

In at least one embodiment, the reducing sugar is selected from the group consisting of: ribose, arabinose, xylose, lyxose, galactose, glucose, mannose, and mixtures thereof. In at least one embodiment, the reducing sugar is fructose or glucose. Sugars and reducing sugars are available from Sigma Aldrich. In at least one embodiment, the reducing sugar is ribose, arabinose, or a mixture thereof. In at least one embodiment, the crosslinking composition comprises a reducing sugar and wherein the reducing sugar is selected from the group consisting of: arabinose, ribose, and mixtures thereof. In at least one embodiment, the crosslinking composition comprises a reducing sugar and wherein the reducing sugar is selected from the group consisting of: D-arabinose, L-arabinose, and mixtures thereof. In at least one embodiment, the reducing sugar is L-arabinose. In at least one embodiment, the sole reducing sugar is a pentose. In at least one embodiment, the sole reducing sugar is selected from the group consisting of: arabinose, ribose, and mixtures thereof. The reducing sugars arabinose, ribose, and mixtures thereof have the benefit of excellent hair straightening performance. By treating hair with reducing sugar and subsequent treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are easily available and thus have economic advantages. In at least one embodiment, the sugar is a reducing sugar and wherein the reducing sugar is selected from the group consisting of: ribose, arabinose, xylose, lyxose, galactose, mannose, and mixtures thereof; or the sugar is arabinose. In at least one embodiment, the crosslinking composition comprises a total amount of reducing sugar being from about 12% to about 18% reducing sugar, and wherein the crosslinking composition comprises arabinose.

Other ingredients may be present in the crosslinking composition. In at least one embodiment, the crosslinking composition comprises antioxidant. Antioxidant is useful in view of providing longer-term stability for the crosslinking composition. In at least one embodiment, the crosslinking composition comprises a safe and effective amount of an antioxidant. In at least one embodiment, the crosslinking composition comprises from about 0.001% to about 5%, or from about 0.5% to about 1.0% antioxidant. In at least one embodiment, the antioxidant is selected from the group consisting of: ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, aminoguanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof. In at least one embodiment, the antioxidant is tocopherol sorbate or an ester of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee. In at least one embodiment, the antioxidant is sodium benzoate. In at least one embodiment, the antioxidant is ascorbic acid. Ascorbic acid has the benefit of enhancing the oxidative stability of the formulation. In at least one embodiment, the crosslinking composition comprises a safe and effective amount of ascorbic acid. In at least one embodiment, the crosslinking composition comprises from about 0.001% to about 5%, or from about 0.5% to about 1.0% ascorbic acid.

In at least one embodiment, the crosslinking composition comprises a chelator or chelating agent. As used herein, "chelator" or "chelating agent" means an agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation. A chelating agent is useful in view of providing longer-term stability for the crosslinking composition. In at least one embodiment, the crosslinking composition comprises a safe and effective amount of a chelator or chelating agent. In at least one embodiment, the crosslinking composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In at least one embodiment, the crosslinking composition comprises a safe and effective amount of chelating agent. In at least one embodiment, the crosslinking composition comprises from about 0.001% to about 10%, or from about 0.01% to about 5%, or from about 0.1% to about 5%, or from about 0.5% to about 1.0% chelating agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. In at least one embodiment, the chelating agent is selected from the group consisting of: N-hydroxysuccinimide deferoxamine, lactoferrin, hydroxamic acids, gluconic acid, phytic acid, derivatives thereof, and mixtures thereof.

In at least one embodiment, the crosslinking composition is in a form suitable for application onto hair. In at least one embodiment, the crosslinking composition is in the form of an emulsion, a solution, or a dispersion. In at least one embodiment, the crosslinking composition comprises a surfactant. The surfactant can be useful in providing an emulsion. In at least one embodiment, when being in the form of an emulsion, said emulsion may be a water-in-oil emulsion, an oil-in-water emulsion, or a multiple emulsion. An emulsion has the benefit of providing an easy-to-apply composition for the consumer to apply to the hair and has aesthetic advantages. The crosslinking composition may be a leave-in composition or a rinse-off composition. The crosslinking composition may be in a form selected from: a shampoo; a hair conditioning composition; a hairstyling composition; or combinations thereof. When being a hairstyling composition, said composition may be a gel composition; a spray gel composition, optionally dispensed using a mechanical spray device and/or at least one propellant; a non-aerosol hairspray, optionally dispensed using a suitable mechanically operated spraying device; a foamable composition, optionally dispensed using devices for foaming; hair wax composition; hair lotion composition; hair cream composition; or combinations thereof. In at least one embodiment, the crosslinking composition is a mascara composition.

The crosslinking composition may further comprise at least one cosmetic hair treatment agent selected from hairstyling polymers, conditioning agents, hair cleansing agents, or mixtures thereof. In at least one embodiment, the crosslinking composition comprises a hairstyling polymer. In at least one embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", $12^{th}$ edition (2008). Suitable hairstyling polymers are, for example, those materials disclosed from page 12, line 5 to page 19, line 1 of the European patent application 08151246.9 filed on 11 Feb. 2008, which is incorporated herein by reference.

In at least one embodiment, the crosslinking composition comprises from about 0.01% to about 10% by weight, or from about 0.1% to about 8%, or from about 0.1% to about 5% hairstyling polymer.

In at least one embodiment, the crosslinking composition comprises a non-ionic hairstyling polymer. In at least one embodiment, the non-ionic hairstyling polymer is a natural or synthetic polymer. In at least one embodiment, the non-ionic hair styling polymers is a polymer obtained from the polymerisation of at least one type of monomer selected from: vinylpyrrolidone; vinylcaprolactam; vinyl esters; vinyl alcohol; vinyl acetate; (meth)acrylamide, and/or its derivatives; (meth)acrylic acid, its salts, and/or its derivatives; propylene and/or ethylene glycol acid; crotonic acid; or mixtures thereof. For example, such polymers are available under the trade names Luviskol® or Luviset Clear®.

In at least one embodiment, the crosslinking composition comprises an anionic hairstyling polymer. In at least one embodiment, the anionic hairstyling polymer is selected from the group consisting of: acrylic acid/alkyl acrylate/ Nalkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/ vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth) acrylate copolymer; ethyl acrylate/methacrylic acid copolymer; vinyl acetate/mono-nbutyl maleate/isobornyl acrylate copolymer; octylacrylamid/(meth)acrylic acid copolymer; polyesters of diglycol, cyclohexanedimethanol, isophthalic acid and sulfoisophthalic acid; and mixtures thereof.

In at least one embodiment, the crosslinking composition comprises a zwitterionic or amphoteric hairstyling polymer. In at least one embodiment, the zwitterionic or amphoteric hairstyling polymer is selected from the group consisting of: alkylacrylamide/alkylaminoalkyl methacrylate/(meth) acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

In at least one embodiment, the crosslinking composition comprises a cationic hairstyling polymer. In at least one embodiment, the cationic hairstyling polymer is selected from the group consisting of homopolymers or copolymers where a quaternary nitrogen groups are present either in the polymer chain or as substituent on one or more of the cationic monomers. The monomers containing ammonium groups may be copolymerized with non-cationic monomers. Suitable cationic monomers may be unsaturated, free-radically polymerizable compounds which carry at least one cationic group, in particular ammonium-substituted vinyl monomers, such as, for example, trialkylmethacryloxyalkylammonium, trialkylacryloxyalkylammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as, for example, C1 to C7-alkyl groups, particularly preferably C1 to C3-alkyl groups. Suitable non-cationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat 755 N; Gafquat 734; Gafquat HS 100; Luviquat HM 550; Merquat Plus 3300; Gaffix VC 713; Aquaflex SF 40. In at least one embodiment, the crosslinking composition comprises a cationic hairstyling polymer derived from a natural polymer. In at least one embodiment, the cationic hairstyling polymer derived from a natural polymer is derived from a natural polymer selected from the group consisting of: cationic derivatives polysaccharides such as cellulose, starch and/or guar; chitosan, its salts, and/or its derivatives; or mixtures thereof. In at least one embodiment, the cationic hairstyling polymers are selected from the group consisting of: polyquaternium-4; polyquatemium-10; polyquaternium-24; guar hydroxypropyltrimonium chloride; chitosonium pyrrolidonecarboxylate; and mixtures thereof.

In at least one embodiment, the crosslinking composition comprises a conditioning agent, or a hair conditioning agent. The crosslinking composition may comprise any suitable and conventional hair conditioning agents. The term "hair conditioning agent" herein means any cosmetically acceptable compound having a cosmetic effect on hair, such as providing gloss to hair, making hair more manageable, improving hair touch, improving combability and/or giving hair more volume. Suitable hair conditioning agents may be found in the CTFA International Cosmetics Ingredient Dictionary and Handbook, "Hair conditioning agents", 12th edition (2008). In at least one embodiment, the hair conditioning agent is selected from the group consisting of: cationic surfactants, non-ionic surfactants, silicone compounds, organic oily conditioning agents, and mixtures thereof. Suitable hair conditioning agents are, for example, those materials disclosed from page 19, line 3 to page 27, line 33 of the European patent application 08151246.9 filed on 11 Feb. 2008, which is incorporated herein by reference.

In at least one embodiment, the conditioning agent is a cationic surfactant. In at least one embodiment, the cationic surfactant comprises amino or quaternary ammonium moieties. In at least one embodiment, the crosslinking composition comprises from about 0.05% to about 3.5%, or from about 0.1% to about 3.0%, or from about 0.5% to about 2.5%, or from about 1.0% to about 2.0% cationic surfactant. In at least one embodiment, cationic surfactant is according to Formula II:

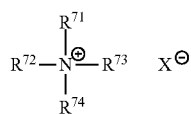

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having from 7 to 22 carbon atoms; wherein the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms; wherein X is selected from the group consisting of: halogen, acetate, citrate, lactate, glycolate, phosphate, nitrate, sulfonate, sulfate, alkylsulfate, alkyl sulfonate radicals, and mixtures thereof. In at least one embodiment, cationic surfactant is according to Formula II (see above), wherein at least one of $R^{71}$, $R^{72}$, $R^{73}$ and $R^{74}$ is an aliphatic group having from 16 to 24 carbon atoms; wherein the remainder of $R^{71}$, $R^{72}$, $R^{73}$ and $R^{74}$ are independently selected from the group consisting of aliphatic groups having from 1 to 4 carbon atoms; wherein X is selected from the group consisting of: chloride or sulfate. In at least one embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group. In at least one embodiment, the cationic surfactant is a di-long alkyl quaternized ammonium salt selected from the group consisting of: dialkyl (14-18 carbons) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof. In at least one embodiment, the cationic surfactant is a tertiary amidoamine having an alkyl group of from about 12 to about 22 carbons. In at least one embodiment, the cationic surfactant is selected from the group consisting of: cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

In at least one embodiment, the conditioning agent is a non-ionic surfactant. Suitable non-ionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

In at least one embodiment, the conditioning agent is a silicone compound. In at least one embodiment, the silicone compound is volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, Dow 5-7113, DC556 Cosmetic Grade Fluid, DC1248 (Dow Corning). In at least one embodiment, the crosslinking composition comprises a conditioning agent being the reaction product of: (a) an aminosilane; (b); polysiloxane; and optionally (c) a polyether. In at least one embodiment, the crosslinking composition comprises a conditioning agent being the reaction product of: (a) an aminosilane; (b); polysiloxane; and (c) a polyether. In at least one embodiment, the crosslinking composition comprises a conditioning agent, and wherein the conditioning agent is selected from the group consisting of: epoxyaminosilane copolymers, and polysiloxane/polyurea block copolymers, and mixtures thereof. In at least one embodiment, the crosslinking composition comprises a conditioning agent being the reaction product of: (a) an aminosilane; (b) polysiloxane; and (c) a polyether; and optionally (d) an amine. In at least one embodiment, the polysiloxane is an epoxy encapped polysiloxane. In at least one embodiment, the polysiloxane comprises at least two oxirane or oxetane groups. In at least one embodiment, the polysiloxane comprises from about 10 to about 450 silicon atoms, or from about 40 to about 400 silicon atoms, from about 75 to about 350 silicon atoms, from about 150 to about 250 silicon atoms. In at least one embodiment, the polysiloxane is an epoxy encapped polysiloxane. In at least one embodiment, the polyether has the average structure $CH_2(O)CHCH_2O(CH_2(CH_3)CH_2O)_nCH_2CH(O)CH_2$ wherein n is an integer from 1 to 10. In at least one embodiment, the amine comprises from 1 to 10 carbon atoms, or from 2 to 5 carbon atoms. In at least one embodiment, the amine is an alkylamine that is substituted with at least one alkyl group. In at least one embodiment, the amine is selected from the group consisting of: methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2,3,3,4,4,5,5,6,6,7,7,8,8,8-pentadecafluoro-1-octanamine, and mixtures thereof. In at least one embodiment, the amine is selected from the group consisting of: methylethylamine, methylhexylamine, methyloctadecylamine, diethanolamine, dibenzylamine, dihexylamine dicyclohexylamine, piperidine, pyrrolidine phthalimide, and mixtures thereof. In at least one embodiment, the conditioning agent is an epoxyaminosilane copolymer. In at least one embodiment, the conditioning agent is conditioning agent being the reaction product of: (a) an aminosilane; (b) polysiloxane, wherein the polysiloxane comprises from about 10 to about 450 silicon atoms, or from about 40 to about 400 silicon atoms; and (c) a polyether; and (d) an amine, wherein the amine is an alkylamine that is substituted with at least one alkyl group. Epoxyaminosilane copolymers are described in EP2214633B1 (filing date 30 Oct. 2008, which is incorporated herein by reference) and are available from Momentive™ Performance Materials Inc., Columbus, Ohio, USA. Epoxyaminosilane copolymers have excellent durability benefits. Such an exemplary expoxyaminosilane copolymer may be synthesised as follows: aminopropyltriisopropoxy silane (40.77 g), an epoxy encapped polysiloxane with the average structure $CH_2(O)CHCH_2OCH_2CH_2Si(CH_3)_2O[Si(CH_3)_2O]_{50}Si(CH_3)_2CH_2CH_2CH_2OCH_2CH(O)CH_2$ (171.40 g) and an epoxy endcapped polyether with the average structure $CH_2(O)CHCH_2O(CH_2(CH_3)CH_2O)_7CH_2CH(O)CH_2$ (37.83 g) and isopropanol (425.68 g) is combined in a 500 mL flask. The material is brought to reflux and stirred with an overhead stirrer. The refluxing continued for 15.5 hr until all epoxy groups are consumed as determined by titration. The material is transferred to a rotary evaporator and stripped at 70° C. and 532 Pa (4 torr) for 2 hrs to remove the isopropanol. Another exemplary expoxyaminosilane copolymer may be synthesised as follows: aminopropyltriisopropoxy silane (14.27 g), 3-(diethylamino)propylamine (7.05 g), an epoxy encapped polysiloxane with the average structure $CH_2(O)CHCH_2OCH_2CH_2CH_2Si(CH_3)_2O[Si(CH_3)_2O]_{200}Si(CH_3)_2CH_2CH_2CH_2OCH_2CH(O)CH_2$ (447.87 g) and an epoxy encapped polyether with the average structure $CH_2(O)CHCH_2O(CH_2CH_2O)_{14}CH_2CH(O)CH_2$ (30.81 g) and isopropanol (500 g) is combined in a 2000 mL flask. The material is brought to reflux and stirred with an overhead stirrer. The refluxing continued for 24 hr until all epoxy groups are consumed as determined by titration. The material is transferred to a rotary evaporator and stripped at 70° C. and 532 Pa (4 torr) for 2 hrs to remove the isopropanol.

In at least one embodiment, the conditioning agent is selected from the group consisting of: epoxyaminosilane copolymers, and polysiloxane/polyurea block copolymers, and mixtures thereof. A polysiloxane/polyurea block copolymer is described in EP2074986B1 filed on 10 Dec. 2008, which is incorporated herein by reference. In at least one embodiment, the polysiloxane/polyurea block copolymer comprises at least one polysiloxane sequence (or block) and at least one polyurea sequence (block) in the backbone of the copolymer. In at least one embodiment, the amount of polysiloxane present in the copolymer is greater than 90% by weight relative to the total weight of the polysiloxane/polyurea block copolymer. In at least one embodiment, the polysiloxane/polyurea block copolymer of the does not comprise polyurethane. By way of non-limiting example, the copolymer can be a non-ionic polysiloxane/polyurea copolymer, that is to say that it does not comprise an ionized or ionizable group. By way of example of a copolymer, non-limiting mention may be made of the dimethylpolysiloxane/polyurea block copolymer having the INCI name polyureadimethicone. Such a dimethylpolysiloxane/polyurea block copolymer can be obtained, for instance, by copolymerization of an α,ω-aminosilicone with a diisocyanate. Polysiloxane/polyurea block copolymers corresponding to these characteristics are, for example, the products sold under the reference Wacker-Belsil® UD 60, Wacker-Belsil® UD 80, Wacker-Belsil® DU 140 and Wacker-Belsil® UD 200 by Wacker. In at least one embodiment, the polysiloxane/polyurea copolymer is non-ionic. In at least one embodiment, the crosslinking composition comprises from about 0.05 to about 20%, for example from 0.1 to 15%, or from 0.5 to 10% polysiloxane/polyurea block copolymer.

In at least one embodiment, the conditioning agent is a polydimethylsiloxane-derivative comprising aminoalkyl groups and having an amine number of at least 0.1 meq/g of polydimethylsiloxane. Such polydimethylsiloxane-derivative can, for example, be methoxy-terminated or hydroxy-terminated, or mixtures thereof. The polydimethylsiloxane-derivative can, for example be a mixture of methoxy- and hydroxy-terminated Poly[3-((2-aminoethyl)amino)propyl]methyl(dimethyl)siloxan as commercially sold under Wacker HC 303.

In at least one embodiment, the conditioning agent is an organic oily conditioning agent. In at least one embodiment, the organic oily conditioning agent is non-volatile, water-insoluble, oily or fatty. Organic oily conditioning agents may be selected from hydrocarbon oils and fatty esters. In at least one embodiment, the conditioning agent is a fatty alcohol. In at least one embodiment, the fatty alcohol is a non-volatile low melting point fatty alcohol. In at least one embodiment, the conditioning agent is a fatty alcohol and the fatty alcohol is selected from the group consisting of: capryl alcohol, lauryl alcohol, stearyl alcohol, cetyl alcohol, myristyl alcohol, palmitoleyl alcohol, and mixtures thereof.

The crosslinking composition may further comprise at least one direct hair dye. In at least one embodiment, the crosslinking composition comprises from about 0.01% to about 15%, or from about 0.1% to about 10%, or from about 0.5% to about 8% direct hair dye.

The crosslinking composition may further comprise at least one viscosity-modifying agent. In at least one embodiment, the crosslinking composition comprises from about 0.01% to about 20%, or from about 0.05% to about 10%, or from about 0.1% to about 5% viscosity-modifying agent.

The crosslinking composition may further comprise at least one emulsifier and/or surfactant. In at least one embodiment, the emulsifier and/or surfactant is selected from non-ionic surfactants; anionic surfactants; amphoretic surfactants; or mixtures thereof. In at least one embodiment, the crosslinking composition comprises from about 0.01% to about 20%, or from about 0.05% to about 10%, or from about 0.1% to about 5%, emulsifier and/or surfactant.

The crosslinking composition may further comprise at least one pigment. In at least one embodiment, the pigment is selected from natural pigments; synthetic pigments; or mixtures thereof. The pigments may be selected from organic pigment, inorganic pigment; or mixtures thereof. The pigments may be selected from coloured pigments; pearlescent pigments; or mixtures thereof. Said crosslinking composition may comprise from about 0.01% to 10%, or from about 1% to about 2% pigment present in the product mass in undissolved form by weight of the total crosslinking composition. The crosslinking composition may comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water-soluble components such as those having C.I. Names.

In at least one embodiment, the crosslinking composition comprises at least one particulate substance. In at least one embodiment, the particulate substance is selected from silica; silicates; aluminates; clay earths; mica; insoluble salts, particularly insoluble inorganic metal salts; metal oxides; minerals; insoluble polymer particles; or mixtures thereof. In at least one embodiment, the crosslinking composition comprises from about 0.01% to about 10%, or from about 0.05% to about 5% of at least one particulate substance. In at least one embodiment, the crosslinking composition is substantially free of a particulate substance such as clay.

In at least one embodiment, the crosslinking composition comprises at least one preservative. In at least one embodiment, the crosslinking composition may comprise from about 0.01% to about 5% by weight, or from about 0.05% to about 1% preservative.

A variety of additional optional ingredients may be incorporated into the crosslinking composition of the present invention. Non-limiting examples of these additional ingredients may be selected from preservatives; antioxidants; sequestering agents; solvents; fragrances & perfumes; fillers; screening agents; odour absorbers; colouring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; colouring agents; polymer plasticizing agents; direct dyes; or mixtures thereof. The crosslinking composition may comprise from about 0%, or from about 0.1% to about 5% antimicrobial agents. In at least one embodiment, the crosslinking composition comprises an organic acid selected from the group consisting of: glycine, L-methionine, L-arginine, biotin, creatine, and mixtures thereof. In at least one embodiment, the crosslinking composition comprises an antidandruff agent. In at least one embodiment, the crosslinking composition comprises zinc pyrithione. In at least one embodiment, the crosslinking composition comprises panthenol. In at least one embodiment, the crosslinking composition comprises a wax compound. In at least one embodiment, the crosslinking composition comprises beeswax.

In at least one embodiment, the crosslinking composition has a viscosity, measured at 25° C., of from about 0.1 mPa·s to about 1,000,000 mPas, or from about 1 mPa·s to about 80,000 mPa·s, or from about 5 mPa·s to about 3,500 mPa·s. The viscosity is measured by HAAKE Rotation Viscometer VT 550 with cooling/heating vessel and sensor systems according to DIN 53019 (MV-DIN, SV-DIN), shear rate is 12.9 s$^{-1}$.

In at least one embodiment, the crosslinking composition is substantially free of: formaldehyde, derivatives of formaldehyde, methylene glycol, formalin, and any compound that produces formaldehyde upon heating. "Heating" means raising the temperature of the compound above 25° C. In at least one embodiment, the crosslinking composition comprises 0% formaldehyde. In at least one embodiment, the derivatives of formaldehyde are 1,3,5-trioxane and paraformaldehyde. In at least one embodiment, the crosslinking composition is substantially free of: formaldehyde, 1,3,5-trioxane, paraformaldehyde, methylene glycol, formalin. Formaldehyde is not preferred in view of its safety profile. Formalin is not advantageous because formalin is a derivative of formaldehyde. Formaldehyde exists in multiple forms. In water, formaldehyde becomes hydrated and forms methylene glycol. A saturated solution of formaldehyde (about 40% formaldehyde) in water is more commonly known as formalin Methanol and/or methylene diol can be used as a stabilizer in formalin and is therefore not advantageous. In at least one embodiment, the crosslinking composition is substantially free of a quaternary ammonium compound and/or a surfactant. In at least one embodiment, the crosslinking composition is substantially free of: ceramide compound, an alpha-hydroxy acid, a thioglycolate and/or thiolactate compound, a bisulfate compound, clay, a reducing agent. In at least one embodiment, the crosslinking composition is substantially free of: ceramide compound, an alpha-hydroxy acid, a thioglycolate and/or thiolactate compound, a bisulfate compound. In at least one embodiment, the crosslinking composition is substantially free of a carbonate compound. In at least one embodiment, the crosslinking composition is substantially free of: ceramide compound, an alpha-hydroxy acid, a thioglycolate or thiolactate compound, a bisulfate compound, clay, formaldehyde, 1,3,5-trioxane, paraformaldehyde, methylene glycol, quaternary ammonium compound, surfactant.

In at least one embodiment, the crosslinking composition has a pH of from about pH 2 to about pH 11. In at least one embodiment, the crosslinking composition has a pH of from about pH 5 to about pH 12, of from about pH 6.5 to about pH 11, or from about pH 8 to about pH 11, or from about pH 9 to about pH 10. In at least one embodiment, the crosslinking composition comprises a buffering agent. In at least one embodiment, the buffering agent is a phosphate buffer. In at least one embodiment, the buffering agent is a borate buffer or a carbonate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia. The buffering agent has the advantage of controlling the pH, which aids the stability of the crosslinking composition. In at least one embodiment, the crosslinking composition comprises an alkalizing agent and/or an agent for adjusting the pH value. The crosslinking composition may further comprise a protonating agent. The protonating agent may be a monoprotic or polyprotic acid, water-soluble or water-insoluble acid, and/or an organic or inorganic acid. In at least one embodiment, the protonating agent is selected from formic acid, acetic acid, sulfuric acid, hydrochloric acid, citric acid, and mixtures thereof. In at least one embodiment, the protonating agent is citric acid. Citric acid is useful because it is naturally available from lemons.

1$^{st}$ Aspect—Method

The first aspect relates to a method for shaping keratin fibres. In at least one embodiment, the method does not comprise a rinsing step. It is not helpful for the efficacy of the invention if the active agent are washed off the keratin fibres prior to mechanically shaping the keratin fibres with an appliance at a temperature of from about 50° C. to about 250° C. In at least one embodiment, the mechanical shaping of keratin fibres is selected from the group consisting of: straightening keratin fibres, such as human scalp hair or human eyelashes, and curling keratin fibres, such as human scalp hair or human eyelashes. In at least one embodiment, the mechanical shaping of keratin fibres is selected from the group consisting of: straightening keratin fibres, such as human scalp hair, and curling keratin fibres, such as human scalp hair or human eyelashes.

The method comprises applying the crosslinking composition to keratin fibres. Further detail on embodiments and description of the crosslinking composition is provided above. In at least one embodiment, the crosslinking composition remains on the keratin fibres for a time X, wherein time X is from about 2 min to about 60 min, or from about 5 min to about 30 min.

The method uses an appliance. In at least one embodiment, the appliance is a hair straightening appliance comprising a heating element. In at least one embodiment, the appliance is a hair curling appliance comprising a heating element. In at least one embodiment, the appliance is a hair straightening appliance comprising a heating element. In at least one embodiment, the appliance is a combing or brushing means.

In at least one embodiment, step (a) is carried out and then subsequently step (b). In at least one embodiment, step (b) comprises (i) applying the crosslinking composition to keratin fibres; and then subsequently (ii) mechanically shaping the keratin fibres with an appliance at a temperature of from about 50° C. to about 250° C. In at least one embodiment, the temperature of the appliance is from about 50° C. to about 250° C., or from about 80° C. to about 180° C. In at least one embodiment, (b) involves elevating the temperature of the appliance to a temperature of from about 50° C., or from about 60° C., or from about 70° C., or from about 80° C. to about 220° C., or to about 200° C., or to about 180° C., or to about 170° C., or to about 160° C., or to about 150° C., or to about 140° C., or to about 130° C. In at least one embodiment, (b) comprises elevating the temperature of the appliance to a temperature of from about 80° C. to about 180° C.

In at least one embodiment, the first aspect relates to a method for shaping keratin fibres comprising:
(a) providing a crosslinking composition, wherein the crosslinking composition comprises:
an active agent, wherein the active agent is 1,3-dioxolan-2-one;
a second active agent being a reducing sugar;
a cosmetically acceptable carrier;
(b) applying the crosslinking composition to keratin fibres, mechanically shaping the keratin fibres with an appliance at a temperature of from about 50° C. to about 250° C.

In at least one embodiment, the crosslinking composition further comprises a viscosity-modifying agent and a conditioning agent. In at least one embodiment, the crosslinking composition has a pH of from about pH 5 to about pH 12, of from about pH 6.5 to about pH 11, or from about pH 8 to about pH 11, or from about pH 9 to about pH 10.

2$^{nd}$ Aspect—Crosslinking Composition

The third aspect relates to a crosslinking composition. A crosslinking composition has been described extensively herein and these features are fully compatible and combinable with the 2$^{nd}$ aspect. In at least one embodiment, the active agent is 1,3-dioxolan-2-one. In at least one embodiment, the crosslinking composition is a solid composition. In at least one embodiment, the crosslinking composition comprises a cosmetically acceptable carrier.

3$^{rd}$ Aspect—Use

The fourth aspect relates to the use of a crosslinking composition for shaping keratin fibres. A crosslinking composition has been described extensively herein and these features are fully compatible and combinable with the 3$^{rd}$ aspect. In at least one embodiment, the use is for straightening keratin fibres. In at least one embodiment, the use is for mechanically shaping keratin fibres. In at least one embodiment, the mechanical shaping of keratin fibres is selected from the group consisting of: straightening keratin fibres, such as human scalp hair or human eyelashes, and curling keratin fibres, such as human scalp hair or human eyelashes.

4$^{th}$ Aspect—Kit

The fourth aspect relates to a kit. The kit comprises a crosslinking formulation comprising the active agent. The active agent has been described extensively herein and these features are fully compatible and combinable with the 4$^{th}$ aspect. In at least one embodiment, the active agent is 1,3-dioxolan-2-one. In at least one embodiment, the crosslinking formulation comprises a cosmetically acceptable carrier. In at least one embodiment, the crosslinking formulation is in liquid form. In at least one embodiment, the crosslinking formulation comprises from about 0.1% to about 99%, or from about 1% to about 98%, or from about 10% to about 97%, or from about 30% to about 95% water. In at least one embodiment, the crosslinking formulation comprises a conditioning agent. Conditioning agents has been described extensively herein and these features are fully compatible and combinable with the 4$^{th}$ aspect. In at least one embodiment, the crosslinking composition has a pH of from about pH 5 to about pH 12, of from about pH 6.5 to about pH 11, or from about pH 8 to about pH 11, or from about pH 9 to about pH 10. In at least one embodiment, the conditioning agent is selected from the group consisting of: epoxyaminosilane copolymers, and polysiloxane/polyurea block copolymers, and mixtures thereof. In at least one embodiment, the crosslinking formulation comprises from about 0.01% to about 10% by weight, or from about 0.1% to about 8%, or from about 0.1% to about 5% hairstyling polymer. In at least one embodiment, the crosslinking formulation is a solid.

The kit comprises an appliance for mechanically shaping keratin fibres. In at least one embodiment, the appliance is a hair brush which is heated. In at least one embodiment, the appliance is hair straightening irons.

In at least one embodiment, the kit further comprises a second formulation comprising a second active agent. In at least one embodiment, the second active agent is a sugar, or a reducing sugar. Sugars and reducing sugars are described herein and this description is compatible with the 5$^{th}$ aspect.

6$^{th}$ Aspect—Process

The sixth aspect relates to a process for forming a crosslinking composition. A crosslinking composition has been described extensively herein and these features are fully compatible and combinable with the 6$^{th}$ aspect. In at least one embodiment, the mixing together is via agitation, for example by stirring.

EXAMPLES

The following examples further describe and demonstrate embodiments within the scope of the present invention. The examples are given solely for the purpose of illustration, and are not to be construed as limitations of the present invention since many variations thereof are possible without departing from its scope.

Example Crosslinking Compositions

|  | A | B | C | D | E (*) | F | G | H |
|---|---|---|---|---|---|---|---|---|
| 1,3-dioxolan-2-one | 5 | 10 | 15 | 10 | 66.58 (10) | — | — | — |
| diethyl carbonate | — | — | — | — | — | 40 | — | — |
| dimethyl carbonate | — | — | — | — | — | — | 5 | — |

-continued

|  | A | B | C | D | E (*) | F | G | H |
|---|---|---|---|---|---|---|---|---|
| diphenyl carbonate | — | — | — | — | — | — | — | 5 |
| arabinose | — | — | — | 10 | — | — | — | — |
| xylose | — | — | — | — | — | — | 5 | — |
| mannose | — | — | — | — | — | — | — | 10 |
| Preservatives[1] | 1 | 1 | 1 | 1 | 6.66 (1) | 1 | 1 | 1 |
| Fragrance | 2 | 2 | 2 | 2 | 13.31 (2) | 1 | 2 | 1 |
| Viscosity-modifying agent[2] | 2 | 2 | 2 | 2 | 13.31 (2) | 2 | 1.5 | 2 |
| Conditioning agent[3] | 1 | 1 | 1 | 1 | 1 | — | 1 | — |
| Deionised water buffered at pH 10[4] | QSP | QSP | QSP | QSP | — (QSP) | — | QSP | QSP |
| Deionised water buffered at pH 10[4] and ethanol (1:1 ratio by volume) | — | — | — | — | — | QSP | — | — |

KEY:
[1] = sodium benzoate;
[2] = Acusol 823 from Rohm and Haas; hydrophobically modified alkali soluble acrylic polymer emulsion (HASE);
[3] = epoxyaminosilane copolymer as described in EP2214633B1 (filing date 30$^{th}$ Oct. 2008) available from Momentive ™ Performance Materials Inc., Columbus, Ohio, USA;
[4] = pH 10 buffer is a standard pH calibration buffer available from suppliers such as VWR, alternatively one can use water and modify the pH. Crosslinking composition E is in solid form;
(*) = wt % after mixing in deionised water.

The crosslinking compositions A-D and F-H are typically at about pH 9-10.

Performance Data

Evaluation of straightening effect: As a measure for the evaluation of the straightening efficacy of a composition according to the present invention, it is possible to employ a hair shape scale that shows the change in shape of the hair after subsequent shampoo washing. If one starts with a curly strand of hair onto which a straight configuration has been impressed as a semi-permanent shape and onto which, is subsequently washed, the progression of the hair shape can be noted on a numbered scale.

Protocol for Preparation & Treatment:
Shampooing: 0.4 ml of shampoo (Pantene® Clarifying Shampoo) is applied to 4 g, 10 inch naturally low lift hair. The shampoo is then gently massaged on hair with fingers for 30 sec.
Rinsing: Hair is thoroughly rinsed with water (at about 36° C.) using a showerhead.
Drying: Hair is dried in a hot box at 140° F. (60° C.) for about 30 min
Treatment: Split hair into 2 sections. Apply 0.5 ml composition according to the present invention to each section. Bring the sections together and apply the remaining product (0.5 ml). In a control experiment (C), water only is applied to each section.
Drying: Heat is applied on the hair using a blow dryer with brushing.
Shaping: Hair is shaped, in this case straightened, using a flat iron at 450° F. (232° C.) with 8 passes.
Protocol: Performance Wash
Shampooing: 4 ml of shampoo (Hairtrition sulfate-free shampoo) is applied onto a hair switch. Hair is gently massaged with fingers for 1.5 min
Rinsing: Hair is thoroughly rinsed with water (about 36° C.) by using showerhead for 2.5 min Hair is then gently pressed together with the hands to drain off the water before wrapping the doll head into a towel and pressing to absorb water.
Combing: Hair is gently combed to mechanically refresh style.
Drying: Hair is blow-dried with diffuser (at about 45° C. for 10 min)
The performance wash may be repeated as often as needed.
Results: Evaluation of the Straightening Efficacy of the Crosslinking Composition:

Following the protocol detailed above, the hair switches are treated so that a semi-permanent style is created. Following shampooing, the hair switches exhibit a change in style and noted on the scale. Referring to FIG. 1, the left hand bar (shaded) shows the straightening efficacy after 1 performance wash and the right hand bar (horizontal stripes) shows the straightening efficacy after 10 performance washes. C=control experiment and 1=after treatment with crosslinking composition of the present invention. Specifically, hair without treatment with the crosslinking composition of the present invention shows less straightening (lower scale) than treated hair with crosslinking composition of the present invention (the active agent is 1,3-dioxolan-2-one).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent publication, is hereby incorporated herein by reference in its entirety unless expressly excluded or otherwise limited. The citation of any document is not an admission that it is prior art with respect to any document disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for mechanically straightening keratin fibres comprising:
   (a) providing a crosslinking composition comprising 1,3-dioxolan-2-one and arabinose, said composition having a pH from 10 to about 12 and a cosmetically acceptable carrier;
   (b) applying the crosslinking composition to keratin fibres, and mechanically straightening the keratin fibres with a hair straightening iron at a temperature of from about 80° C. to about 250° C.;
   wherein said method is conducted without the use of thioglycolic acid or hydrogen peroxide; wherein said crosslinking composition is substantially free of: formaldehyde, derivatives of formaldehyde, formalin, and any compound that produces formaldehyde upon heating.

2. The method of claim 1, wherein the crosslinking composition comprises a conditioning agent being the reaction product of: (a) an aminosilane; (b) polysiloxane; and optionally (c) a polyether.

3. The method of claim 1, wherein the method does not comprise a rinsing step.

* * * * *